United States Patent [19]

Raison et al.

[11] Patent Number: 5,077,391
[45] Date of Patent: Dec. 31, 1991

[54] PURIFICATION OF IMMUNOGLOBULIN M

[76] Inventors: Robert L. Raison, School of Biological and Biomedical Sciences University of Technology, Sydney Westbourne St., Gore Hill, NSW 2065; Simon B. Easterbrook-Smith, 128 Lucinda Avenue, Wahroonga NSW 2076; Andrew G. Nethery, 24 Hamersley Street, Fairfield West, 2165, all of Australia

[21] Appl. No.: 444,547

[22] Filed: Dec. 1, 1989

[51] Int. Cl.$^5$ .......................... C07K 3/20; C07K 3/28; C07K 15/00; C07K 15/14

[52] U.S. Cl. .................................... 530/387; 530/413; 530/808; 530/809; 530/830

[58] Field of Search ................ 580/387; 500/809, 808, 500/413, 830

[56] References Cited

U.S. PATENT DOCUMENTS 4,704,366 11/1987 Juarez-Salinas et al. ........... 530/387
4,882,423 11/1989 Taguchi et al. ..................... 530/380

OTHER PUBLICATIONS

Svehag, S-E., and D. Burger, (1976), Isolation of C1q Binding Immune Complex..., Arch. Phys. Med. Rehabil. 57:45–52.

Casali, P., and P-H. Lambert, (1979), Purification of Soluble..., Clin. Exh. Immunol. 37(2):295–309.

Diwan, J. J. et al., (1987), Interaction of Quinine with Mitochondrial K+ Transport..., Adv. Memb. Biochem. Bioenerg., Kim et al. (editors), p. 405.

Gibbons et al., Biochimica et. Biophys. Acta, vol. 670 (1981), pp. 146–149.

Svahag et al., Acta. Path. Microbiol. Scand. Sect. C (1976), vol. 84, pp. 45–52.

Primary Examiner—Howard E. Schain

[57] ABSTRACT

Immunoglobulin M is purified by absorption upon an insoluble matrix material having chemically bound thereon the protein C1q. The matrix is washed and purified immunoglobulin M is then released from the matrix.

12 Claims, 3 Drawing Sheets

FIG. 1a

```
          1         10*        20*        30*        40
A chain   E D L C R A P D G K K G E A G R P G R R R G R P G L K G E Q G E P G A P G I R T G I
                    Q - - - G L K G D Q G E P
                            50*
B chain   E L S C T G P P A I P G I P G T P G P D G Q P G T P G I K G E K G L P - G L
          A G D H G E F G E K G D P
                                    *
C chain   N T G C Y G I P G M P G L P A A P G K D G Y D G L P P G P P G E P G I P A I K - G I
          R - - - G P P G Q K G E P
                   60*                                    80*         90
A chain   G P S G N P G K V G Y P G P S G P L G A R G I K G I K G T P G S P G N I K D Q P R
          P A F S A I R R - N P P M
              100
B chain   G I P G D P G K V G P K G P M G P K G I P G A P G A P G P K G E S G D Y K A T Q K
          I A F S A T R T I N V P L
                                                          *
C chain   G L P G H K G K D G P N G P P G M P G V P G P M G I P G E E P G E E G R [Y K Q K F Q]
          S V F T V T R A P Q L P A
                          Q T
```

FIG.1b

```
         110              120              130              140
A-chain  G G N V V I R F D T V I T N Q E E P Y Q N H S G R F V C T V P G Y Y Y F T F Q V L
                        150                      160
                        Q W E I
B-chain               S      N L S I V S W S - R  R R D Q T I R P D H V I T N M N N N Y E P R S G K F T C K V P G L Y Y F T Y H A S
                                                  S R G N L C V N L M R G R
                     Y
                     G                            170              180
C-chain  - N H S I R F N A V L T N P Q G D Y D T S T G K F T C K V P G L Y Y F V V Y H A L
         S T A N L L V (L L X X X) R 190              200
                                                                                    G L
A-chain  G Q V R R S L G F C D T T N K   F Q V V S G G M V L Q L Q Q G D Q V W V E K D P K
                                         210
                                         S E
B-chain  E R A Q K V V T F C D Y A Y N T F Q V T T G G M V L K L E Q G E N V F L Q A T D K
         K G H I Y Q G       A D S V F
         N S L L G M E G A N S I F
C-chain  - S G V K V V T F C G H T S K T N Q V N S G G V L L R L Q H G E E H W L A V N D Y
         Y I M V G I Q G D S V F
```

```
         220              226
A-chain  S G F I L - P G F S A
B-chain  S G F L L F P D M E A
C-chain  S G F L L F P D
```

FIG. 1c

PURIFICATION OF IMMUNOGLOBULIN M

FIELD OF INVENTION

The present invention relates to the purification of immunoglobulin M (IgM), and is particularly applicable to the purification in a rapid and efficient manner of crude samples such as serum or fluids produced through the application of monoclonal-antibody technology (ascites or culture supernatant).

BACKGROUND OF THE INVENTION

IgMs produced by monoclonal-antibody technology are used as reagents with applications throughout medicine and biotechnology.

Affinity chromatography, using immobilized Protein A, is widely used to purify immunoglobulin G (IgG) from sources such as hybridoma culture supernatant or ascites fluid. Equally rapid and convenient methods for purifying immunoglobulin M are not generally available in spite of a long felt commercial and research need for such a method. An object of the instant invention is to provide for a rapid, reliable and convenient method for isolation of IgM. An additional object of the instant invention is to provide for a convenient assembly of components (i.e. a kit) which would allow a researcher in the arena of immunology to easily and rapidly practice the invention described herein.

SUMMARY OF THE INVENTION

A method for isolation and purification of Immunoglobulin M (IgM) from an aqueous sample containing the sought for IgM together with various impurities comprising the steps of:

a) mixing an impure, IgM containing fluid with an insoluble hydrophilic matrix whereon said matrix the protein Clq is chemically bound thereby resulting in formation of a IgM-Clq-insoluble matrix;

b) washing the IgM-Clq-insoluble matrix complex with an aqueous wash buffer;

c) releasing the purified IgM from the IgM-Clq-insoluble matrix

Preferably, the impure IgM containing fluid is mixed with the insoluble hydrophilic matrix at a temperature of about 2-10° C., more preferably 5° C.

It is preferable that the washing of the IgM-Clq-insoluble matrix complex with the aqueous wash buffer is carried out at a temperature of about 2-10° C.

Preferably, the releasing of the purified IgM from the IgM-Clq-insoluble matrix is performed by either of the following methods:

a) mixing the washed IgM-Clq-insoluble matrix complex with fresh aqueous wash buffer, raising the temperature of the wash buffer to room temperature, preferably 17-25° C., thereby dissociating the IgM from the insoluble matrix complex; or b) by incorporating potassium iodide, for example, 0.5M into the wash buffer, at a preferred temperature of about 2-10° C., more preferable 5° C.

Also provided is kit useful for isolation of purified IgM. The kit includes a chromatographic column containing insoluble hydrophilic particles having chemically bonded thereto the protein Clq, and a supply of aqueous wash buffer. Preferably, the kit also contains an aqueous elution buffer consisting of wash buffer containing 0.5M KI.

BRIEF DESCRIPTION OF DRAWING

FIG. 1 shows the amino-acid sequences of the three chain types (A, B and C) of human Clq, specified by the single-letter amino acid code. This information is contained in Reid K.B.M. (1988) "The Clq Complex" in "Biochemistry and Molecular Biology of Complement" (ed. Sim. R.B.) MTP Press Ltd., Lancaster, U.K. This publication is currently in press."

DESCRIPTION OF THE INVENTION

The protein Clq is a well known, serum glycoprotein of approximate molecular weight $410 \times 10^3$. It is part of a system of proteins in serum called complement, which in turn, is an important feature of the immune system. Clq is comprised of 18 polypeptide chains; six each of three types denoted A, B, and C, which are of similar, unusual structure. (See FIG. 1) A collagen-like repeating sequence of amino-acids comprises the 80 or so amino-terminal residues. The remaining amino-acid sequences form a globular protein conformation which contains a region which binds the $F_c$ portions of immunoglobulins M and G. The identity of the amino acid residues comprising a IgM binding site are not known with certainty, but are thought to lie between residues 90 and 226, within the non-collagenous portions of Clq. The amino-acid sequences of the three chain types of Human Clq has been described and is contained in Reid, K.B.M. (1988) "The Cl complex" in "Biochemistry and Molecular Biology of Complement" (ed. Sim, R.B.) MTB Press Ltd., Lancaster, UK. (In press)

Additionally well known are procedures for isolating Clq from human serum in reasonably pure form such as the method of Tenner, et al, (1981) in Journal of Immunology 127, 648-653 which is further described in the examples of this disclosure. It is well known by those skilled in the art that Clq from other than a human serum source or from a recombitant source are equivalent options.

The art of affinity chromatography is a well known and frequently employed method for purification of biomolecules. In brief, the method of affinity chromatography makes use of an "affinity ligand" chemically attached to an insoluble, carrier matrix. By design, the affinity ligand is chosen on the basis of its ability to exhibit some interactive or affinity ability with some target molecule such that the target molecule can be specifically rendered insoluble thereby removing it from contaminating impurities which remain in solution.

With respect to the insoluble matrix, there are several, commercially available options available to the practitioner of affinity chromatography. Preferably, the instant disclosure employs the beaded, polymeric, insoluble hydrophilic matrix agarose which is commercially available under the tradename Sepharose by the Pharmacia-LKB Company. There are also other suitable commercially available affinity chromatography materials, including beaded forms of cross-linked acrylamide, activated agarose beads (e.g. Affigel sold by BioRad) and macroporous polymers (e.g. AffiPrep sold by BioRad).

With respect to the method of chemically attaching the affinity ligand to the insoluble matrix, the practitioner of affinity chromatography again has several options available and the choice is often a matter of convenience. Preferably, the instant disclosure employs the commercially available cyanogen bromide activated agarose (CNBr-activated Sepharose made by Pharmacia-LKB).

In practice, the present invention employs the protein Clq as an affinity ligand after it has been chemically attached (immobilized) to a hydrophilic, insoluble matrix. IgM contained in an impure sample is bound to the Clq-insoluble matrix at reduced temperature e.g. 2 to 10° C., preferably around 5° C.. The IgM bound to the Clq-insoluble matrix may then be released simply and isocratically (i.e. without changing the buffer composition) by raising the temperature to room temperature and eluting with the same buffer. Alternatively, the IgM may be eluted by washing with buffer containing potassium iodide (e.g. 0.5M KI).

The following examples serve to illustrate at least the preferred embodiments of the present invention. The Examples are not intended to limit the scope of the invention in any way.

EXAMPLE 1

Preparation of Clq affinity ligand

Preparation of purified Clq affinity ligand used for preparation of an insoluble Clq-matrix may be accomplished according to the method of Tenner et al. (1981) Journal of Immunology volume 127, pages 648–653. Specifically, approximately 1.0 liter of Human serum is made 5mM in ethylene diamine tetraacetic acid, sodium salt (EDTA) and applied to a 400ml column of cation exchange resin which has been equilibrated with 50mM phosphate, 82mM NaCl, 2mM EDTA, pH 7.2 loading buffer (commercially available cation exchange resin sold under the tradename Bio-Rex-70 by the BioRad company is suitable). After the entire amount of human serum has been applied to the column, the column is washed with loading buffer to remove proteins not bound to the cation exchange resin. Washing is accomplished by allowing the loading buffer to flow through the resin, preferably said resin is contained in a chromatographic column. Washing is continued until the UV absorbance of the eluate contained in a 1cm cell is less than 0.10 absorbance units at 280nm. Elution of the desired Clq fraction from the cation exchange resin is accomplished by applying a linear NaCl gradient to the washed chromatographic column, monitoring the eluate by absorbance at 280nm or immunologically, pooling Clq fractions and precipitating the Clq by rendering the positive fractions 33% saturated in ammonium sulfate. The precipitated protein fraction at this point is approximately 80% pure and may be collected by centrifugation. Following dialysis vs column loading buffer described above, the isolated Clq may be used directly for preparation a matrix described in example 2 or further purified by size exclusion chromatography employing a 90 x 2.5cm column of Sephacryl ™ S-300 equilibrated with 50mM tris(hydroxymethyl)aminomethane (tris), 500mM NaCl, 2mM EDTA. The yield of Clq following the two-step purification procedure described here is typically 50mgs when starting with 1 liter of serum.

EXAMPLE 2

Preparation of Clo affinity matrix

Cyanogen bromide activated Sepharose ™ 4B obtainable from the Pharmacia-LKB Company is washed and swollen on a sintered glass filter with 1mM HCl, using 200 ml of HCl per gram of Sepharose ™ powder.

Purified Clq as from EXAMPLE 1 is dissolved in either 0.5M NaCl containing 5mM sodium succinate or 0.5M NaCl containing 0.1M NaHCO3, pH 8.3 at a protein concentration of 3 mg/ml. For each ml of swollen, washed cyanogen bromide activated gel is mixed 2ml (5-6mg) of the Clq solution and the entire mixture is allowed to gently agitate overnight at 50° C. in an end-over-end mixer or the like.

The gel is then transferred to 0.2M glycine, pH 8 buffer for mixing end-over-end at room temperature for 2 hours. The gel is then washed several times alternately with 0.1M sodium acetate, pH 4, 0.5M NaCl, followed by 0.1M NaHCO3 pH 8.3, 0.5M NaCl.

The immobilized Clq obtained is then packed into a chromatography column and washed with 50 mM sodium phosphate, pH 7.2, 150 mM NaCl, 1mM phenylmethylsulfonyl fluoride (PMSF), 0.02% (w/v) sodium azide. This buffer is referred to as "column buffer". The Clq-matrix thus obtained and configured in a chromatography column is stable in this buffer until used in EXAMPLE 3. The capacity of immobilized Clq to bind IgM is at least 0.4mg per ml of matrix. The capacity of the column and the purity of IgM produced by it are not affected by at least 18 months storage in column buffer at 50° C.

EXAMPLE 3

Purification of IcM

Suitable samples for this example are any solutions containing IgM in significant amounts, such as mouse monoclonal IgM ascites fluid or human myeloma serum. These two examples have been used successfully for the purification of IgM, however any IgM containing sample should suffice. Since the Clq-IgM interaction occurs freely across mammalian species boundaries, the species of origin of either Clq or IgM is not crucial.

Samples are brought to pH 7.2, 10mM EDTA, 0.1 mM PMSF, and 0.02% sodium azide and clarified by centrifugation. The samples are then applied to the Clq-matrix column at a flow rate of 0.5 ml/minute at 50C. The column is washed with column buffer at a flow rate of 0.5 ml/minute at 50° Cm until the absorbance (280 nm) of the wash eluate returns to baseline.

The flow is stopped and the column is incubated at room temperature (17-25° C.) for 2 hours. The column is then further eluted with column buffer at room temperature and the UV absorbance at 280 nm of the eluate is monitored. The protein eluting in the volume of buffer which had been contained in the column is purified IgM. As an alternative to isocratic, 17-250C. elution of IgM, bound IgM may be eluted at 50° C. by washing the column with column buffer containing 0.5M KI.

IgM produced by the examples cited herein is of very high purity with only minor contaminants detectable by electrophoresis or immunodiffusion analysis which is in stark contrast to the crude starting materials.

EXAMPLE 4.

Assembly of an IqM Purification kit

Clq affinity matrix (part by volume)prepared as in EXAMPLE 2 is mixed with approximately 1-2 parts by volume of of "column buffer" described in EXAMPLE 2 to form a 33-50% v/v slurry of matrix in buffer. The obtained slurry is poured into an empty, preferably "disposable" chromatographic column equipped with a bottom filter frit of sufficient porosity to allow liquid to pass through while retaining the particulate affinity matrix. The column is also equipped with both bottom and top removable caps such that the entire configuration can be shipped in a container without loss or leakage of the column contents. Disposable columns are commercially available from a number of laboratory supply houses e.g. "disposable polystyrene columns" product number 29920 from Pierce Chemical Co., Rockford, Illinois, USA that are suitable for use in this example. Additional preferred components of a kit useful for isolation of IgM according to the instant invention are a supply of pre-formulated column buffer made according to EXAMPLE 2 packaged in a suitable container and optionally, a supply of this same column buffer containing 0.5M KI.

What is claimed is:

1. A method for isolation and purification of Immunoglobulin M (IgM) from an aqueous sample containing the sought for IgM together with various impurities comprising the steps of:
   a) mixing an impure, IgM containing fluid with an insoluble hydophilic matrix whereon said matrix the protein Clq is chemically bound thereby resulting in formation of a IgM-Clq-insoluble matrix;
   b) washing the IgM-Clq-insoluble matrix complex with an aqueous wash buffer;
   c) releasing the purified IgM from the IgM-Clq insoluble matrix.

2. The method as claimed in claim 1, wherein the impure IgM containing fluid is mixed with the insoluble hydrophilic matrix at a temperature of about 2-100° C.

3. A method as claimed in claim 1, wherein the washing of the IgM-Clq-insoluble matrix complex with the aqueous wash buffer is carried out at a temperature of about 2-100° C.

4. A method as claimed in claim 1, wherein the releasing of the purified IgM from the IgM-Clq-insoluble matrix is performed by mixing the washed IgM-Clq-insoluble matrix complex with fresh aqueous wash buffer, raising the temperature of the wash buffer to room temperature thereby dissociating the IgM from the insoluble matrix complex.

5. A method as claimed in claim 4, wherein the wash buffer temperature is raised to about 17-25OC. for about 2 hours.

6. A method as claimed in claim 1, wherein the releasing of the purified IgM from the IgM-Clq-insoluble matrix is performed by incorporating potassium iodide into the wash buffer.

7. A method as claimed in claim 6, wherein 0.5M potassium iodide is incorporated into the wash buffer.

8. A method as claimed in claim 6, wherein the releasing of the purified IgM is performed at a temperature of about 2-100° C.

9. The method of claim 1 wherein the insoluble hydrophilic matrix having the protein Clq chemically bonded thereto consists of beaded agarose.

10. The method of claim 1, wherein the steps of IgM binding, washing and releasing are accomplished in a chromatographic column.

11. The method of claim 1 wherein the aqueous sample is mouse monoclonal IgM ascites fluid or human myeloma serum.

12. The method of claim 11 wherein the aqueous sample is human myeloma serum.

* * * * *